United States Patent
Efcavitch et al.

(10) Patent No.: US 10,982,276 B2
(45) Date of Patent: Apr. 20, 2021

(54) HOMOPOLYMER ENCODED NUCLEIC ACID MEMORY

(71) Applicant: Molecular Assemblies, Inc., San Diego, CA (US)

(72) Inventors: J. William Efcavitch, San Carlos, CA (US); Matthew T. Holden, San Diego, CA (US)

(73) Assignee: Molecular Assemblies, Inc., San Diego, CA (US)

( * ) Notice: Subject to any disclaimer, the term of this patent is extended or adjusted under 35 U.S.C. 154(b) by 0 days.

(21) Appl. No.: 15/994,335

(22) Filed: May 31, 2018

(65) Prior Publication Data

US 2019/0040459 A1    Feb. 7, 2019

Related U.S. Application Data

(60) Provisional application No. 62/513,111, filed on May 31, 2017.

(51) Int. Cl.

| | |
|---|---|
| *C12Q 1/6869* | (2018.01) |
| *G06N 3/12* | (2006.01) |
| *G11B 7/245* | (2006.01) |
| *G11C 7/00* | (2006.01) |

(52) U.S. Cl.
CPC ........... *C12Q 1/6869* (2013.01); *G06N 3/123* (2013.01); *G11B 7/245* (2013.01); *G11C 7/00* (2013.01)

(58) Field of Classification Search
CPC .............................. C12Q 1/6869; G06N 3/123
See application file for complete search history.

(56) References Cited

U.S. PATENT DOCUMENTS

| | | |
|---|---|---|
| 2012/0160681 A1 | 6/2012 | Davis et al. |
| 2016/0046974 A1 | 2/2016 | Efcavitch et al. |
| 2017/0017436 A1 | 1/2017 | Church |
| 2017/0121766 A1 | 5/2017 | Schultz et al. |

FOREIGN PATENT DOCUMENTS

| | | | |
|---|---|---|---|
| WO | 2017151680 A2 | | 9/2017 |
| WO | 2018094115 A1 | | 5/2018 |
| WO | WO 2018/094115 | * | 5/2018 |
| WO | 2018132457 A1 | | 7/2018 |

OTHER PUBLICATIONS

Mayer et al, An Epigenetics-Inspired DNA-Based Data Storage System, 2016, Angew. Chem. Int. Ed., 55, 11144-11148 (Year: 2016).*
Mayer et al, An Epigenetics-Inspired DNA-Based Data Storage System, 2016, Angew. Chem. Int. Ed., 55, 11144-11148, Supplemental information, pp. 1-229. (Year: 2016).*
Hogg, Matthew et al., "Promiscuous DNA Synthesis by Human DNA Polymerase q," Nucleic Acids Research, Nov. 30, 2011, vol. 40, Issue 6, pp. 2611-2622 (12 Pages).
International Search Report and Written Opninion of the International Searching Authority dated Oct. 15, 2018 for International Application No. PCT/US2018/035365 (16 Pages).
Pud, Sergii et al., "Mechanical Trapping of DNA in a Double-Nanopore System," Nano Letters, Dec. 1, 2016, vol. 16, No. 12, pp. 8021-8028 (17 Pages).
Zakeri, Bijan et al., "Multiplexed Sequence Encoding: A Framework for DNA Communication," PLoS One, 06 Aoruk 2016, vol. 11, No. 4, pp. 1-27 (27 Pages).
Mayer et al, An Epigenetics-Inspired DNA-Based Data Storage System, 2016, Angew. Chem. Int. Ed., 55, 11144-11148.

* cited by examiner

*Primary Examiner* — Narayan K Bhat
(74) *Attorney, Agent, or Firm* — Brown Rudnick LLP; Thomas C. Meyers

(57) ABSTRACT

Nucleic acid memory strands encoding digital data using a sequence of homopolymer tracts of repeated nucleotides provides a cheaper and faster alternative to conventional digital DNA storage techniques. The use of homopolymer tracts allows for lower fidelity, high throughput sequencing techniques such as nanopore sequencing to read data encoded in the memory strands. Specialized synthesis techniques allow for synthesis of long memory strands capable of encoding large volumes of data despite the reduced data density afforded by homopolymer tracts as compared to conventional single nucleotide sequences.

8 Claims, 11 Drawing Sheets

Specification includes a Sequence Listing.

| Base n | Homopolymer Length | Strand Length | # Strands/GB | Base n | Homopolymer Length | Strand Length | # Strands/GB | Base n | Homopolymer Length | Strand Length | # Strands/GB |
|---|---|---|---|---|---|---|---|---|---|---|---|
| 2 | 2 | 500 | 3.2E+07 | 2 | 5 | 500 | 8.0E+07 | 2 | 10 | 500 | 1.6E+08 |
| 4 | 2 | 500 | 1.6E+07 | 4 | 5 | 500 | 4.0E+07 | 4 | 10 | 500 | 8.0E+07 |
| 6 | 2 | 500 | 1.2E+07 | 6 | 5 | 500 | 3.1E+07 | 6 | 10 | 500 | 6.2E+07 |
| 8 | 2 | 500 | 1.1E+07 | 8 | 5 | 500 | 2.7E+07 | 8 | 10 | 500 | 5.3E+07 |
| 12 | 2 | 500 | 8.9E+06 | 12 | 5 | 500 | 2.3E+07 | 12 | 10 | 500 | 4.5E+07 |
| 16 | 2 | 500 | 8.0E+06 | 16 | 5 | 500 | 2.0E+07 | 16 | 10 | 500 | 4.0E+07 |

| Base n | Homopolymer Length | Strand Length | # Strands/GB | Base n | Homopolymer Length | Strand Length | # Strands/GB | Base n | Homopolymer Length | Strand Length | # Strands/GB |
|---|---|---|---|---|---|---|---|---|---|---|---|
| 2 | 2 | 1000 | 1.6E+07 | 2 | 5 | 1000 | 4.0E+07 | 2 | 10 | 1000 | 8.0E+07 |
| 4 | 2 | 1000 | 8.0E+06 | 4 | 5 | 1000 | 2.0E+07 | 4 | 10 | 1000 | 4.0E+07 |
| 6 | 2 | 1000 | 6.2E+06 | 6 | 5 | 1000 | 1.5E+07 | 6 | 10 | 1000 | 3.1E+07 |
| 8 | 2 | 1000 | 5.3E+06 | 8 | 5 | 1000 | 1.3E+07 | 8 | 10 | 1000 | 2.7E+07 |
| 12 | 2 | 1000 | 4.5E+06 | 12 | 5 | 1000 | 1.1E+07 | 12 | 10 | 1000 | 2.3E+07 |
| 16 | 2 | 1000 | 4.0E+06 | 16 | 5 | 1000 | 1.0E+07 | 16 | 10 | 1000 | 2.0E+07 |

| Base n | Homopolymer Length | Strand Length | # Strands/GB | Base n | Homopolymer Length | Strand Length | # Strands/GB | Base n | Homopolymer Length | Strand Length | # Strands/GB |
|---|---|---|---|---|---|---|---|---|---|---|---|
| 2 | 2 | 10000 | 1.6E+06 | 2 | 5 | 10000 | 4.0E+06 | 2 | 10 | 10000 | 8.0E+06 |
| 4 | 2 | 10000 | 8.0E+05 | 4 | 5 | 10000 | 2.0E+06 | 4 | 10 | 10000 | 4.0E+06 |
| 6 | 2 | 10000 | 6.2E+05 | 6 | 5 | 10000 | 1.5E+06 | 6 | 10 | 10000 | 3.1E+06 |
| 8 | 2 | 10000 | 5.3E+05 | 8 | 5 | 10000 | 1.3E+06 | 8 | 10 | 10000 | 2.7E+06 |
| 12 | 2 | 10000 | 4.5E+05 | 12 | 5 | 10000 | 1.1E+06 | 12 | 10 | 10000 | 2.2E+06 |
| 16 | 2 | 10000 | 4.0E+05 | 16 | 5 | 10000 | 1.0E+06 | 16 | 10 | 10000 | 2.0E+06 |

FIG. 4

HOMOPOLYMER ENCODED NUCLEIC ACID MEMORY

RELATED APPLICATIONS

The present application claims the benefit of and priority to U.S. provisional patent application Ser. No. 62/513,111, filed May 31, 2017, the content of which is incorporated by reference herein in its entirety.

FIELD OF THE INVENTION

The invention relates to methods and apparatus for storing data in a nucleic acid memory strand comprising homopolymer tracts.

BACKGROUND

DNA digital storage is a process of representing digital data using the base sequences of DNA and storing that data through DNA synthesis of polynucleotides corresponding to the base sequence encoding the data. DNA digital storage provides several advantages over conventional data storage methods and targets a market in the tens of billions of dollars. Conventional data storage methods including flash memory and recording on magnetic tapes pose problems related to physical space requirements, reliance on scarce resources, and data integrity. DNA digital storage provides much greater data storage density with significantly lower energy requirements. Current methods rely on high-fidelity sequencing techniques with little tolerance for errors in order to accurately read the data encoded in the DNA. The required sequencing methods are relatively slow and expensive to meet the fidelity requirements. An example of current DNA digital storage techniques is described in U.S. Pat. No. 9,384,320 to Church, et al. (incorporated herein by reference). In order to increase sequencing fidelity, current methods such as those described by Church encode data using sequences that avoid features that are difficult to read or write such as sequence repeats.

The synthesis side of current DNA digital storage techniques further limits adoption of the technology through a lack of speed, production of toxic byproducts, and high costs. Most de novo nucleic acid sequences are synthesized using solid phase phosphoramidite-techniques that involve the sequential de-protection and synthesis of sequences built from phosphoramidite reagents corresponding to natural (or non-natural) nucleic acid bases. While inkjet synthesis on array-based formats is capable of very low cost phosphoramidite synthesis, the strands that are made are limited to 100-200 bases in length, must sacrifice some of the length to index sequences, and are made in sub-femtomolar scale requiring post-synthesis amplification to provide sufficient material for subsequent read-out. Using conventional synthesis techniques, nucleic acids greater than 200 base pairs (bp) in length experience high rates of breakage and side reactions. Additionally, conventional synthesis techniques produce toxic by-products, and the disposal of this waste limits the availability of nucleic acid synthesizers and increases the costs of oligo production. These complications related to synthesis and read-out in DNA digital storage have limited the applications for an otherwise promising technology.

SUMMARY

The invention provides systems and methods for storing data using sequences of homopolymer tracts encoding digital data. Representing each bit in the data sequence using a homopolymer tract of repeated bases (e.g., 2-10 nucleotides) allows for higher throughput and less expensive sequencing techniques to be used. Because the sequence read relies only on discriminating the transition between homopolymer tracts and does not require a faithful read of each individual nucleotide, sequencing techniques such as nanopore sequencing, zero-mode waveguide (ZMW) single molecule sequencing, and mass spectrometry may be used to increase speed and reduce cost.

Recording of data using homopolymer tracts as described herein is most efficiently accomplished using long strands (e.g., 5-10 kb) of nucleic acid. While traditional synthesis techniques are length limited, template-independent polynucleotide synthesis of using, for example, a nucleotidyl transferase are capable of synthesizing long strands at reduced costs and with lower waste production. Enzymatically synthesized ssDNA memory strands only require 50% of the DNA synthesis compared to conventional phosphoramidite approaches because ssDNA strands longer than about 100-200 nucleotides in length require complex and costly ligation or PCR techniques and can only produce ssDNA from dsDNA intermediates. See, U.S. Pat. No. 8,808,989 to Efcavitch, et al., incorporated herein by reference. Data encoding can be in numerical base 2, 3, 4 using standard nucleotides or data density can be increased using any number of modified nucleotide analogs to generate base 8, 10, 12, or more encoding schemes.

The limitations on modified nucleotide analogs are only that they can be incorporated using the chosen synthesis technique (e.g., terminal deoxynucleotidyl transferase (TdT)) and can be differentiated from one another using the chosen sequencing analysis. In some embodiments, synthesis may be accomplished using polymerase theta in the presence of $Mn^{2+}$.

Consistent homopolymer tract length is not essential to the systems and methods of the invention because it is only the transition between individual tracts that needs to be recognized. Even though the tract length can be allowed to vary, synthesis techniques of the invention can effectively control the average homopolymer tract length by adjusting the ratio of deoxynucleotides (dNTPs) to the oligonucleotide memory strands being synthesized and controlling the exposure time of the dNTPs to the nascent memory strand. The length of the homopolymer tracts can be optimized to the readout technology; the highest data storage density is achieved with single nucleotide readout resolution, but the highest readout speed and accuracy are achievable by expanding the size of the nucleotide bit to the minimum detectable length (e.g., 2-10 nucleotides) for a given sequencing technology.

Systems and methods of the invention that use nanopore sequencing may use specialized memory strand constructs such as stoppers (e.g., hairpins or macromolecular appendages) included on one or both ends of the strand. In other nanopore-based methods, the memory strand may be circularized and threaded between adjacent nanopores.

Certain aspects of the invention include a method of recording data using a nucleic acid memory strand. Steps of the method may include creating an in-silico oligonucleotide sequence that represents a dataset where each nucleotide of the oligonucleotide sequence corresponds to a unit of said dataset. A nucleic acid memory strand can then be synthesized comprising a plurality of homopolymer tracts where each homopolymer tract corresponds to a nucleotide of the oligonucleotide sequence. The plurality of homopolymer tracts may include between 3 and 10 repeated nucleotides.

Each unit of said dataset can be represented in base 2, base 3, base 4, or higher as desired for a particular application.

In certain embodiments, the nucleic acid memory strand may be from at least about 200 nucleotides in length to about 5,000 nucleotides in length. The synthesizing step may include controlling homopolymer length by varying dNTP concentration. Steps of the method may include modifying a first end of the nucleic acid memory strand to prevent passage of the first end through a nanopore of a nanopore sequencing system; passing a second end of the nucleic acid memory strand through the nanopore; and modifying the second end of the nucleic acid memory strand to prevent passage of the second end through the nanopore.

Other embodiments may utilize a memory strand be comprised of heteropolymer tracts of a defined stoichiometry or composition to further increase the coding capacity of a set number of nucleotide analogs. Further embodiments may seek to protect the data encoded in a memory strand by using nucleotide analogs that are similar in structure but employ linkers that can be removed under different conditions such as ultraviolet or visible light, oxidizing or reducing agents, alkaline or acidic pH, or sequence specific nucleases, thereby disguising the data to those without knowledge of the applicable process.

The dataset may be selected from the group consisting of a text file, an image file, and an audio file. The synthesizing step may include template-independent synthesis. In certain embodiments, a nucleotidyl transferase enzyme may be used to catalyze said template-independent synthesis. Polymerase theta can be used to catalyze said template-independent synthesis in some embodiments.

Aspects of the invention may include a method of reading data from a nucleic acid memory strand. Steps of the method can include sequencing a nucleic acid memory strand comprising a plurality of homopolymer tracts; converting the nucleic acid memory strand sequence into digitized data, wherein each of the plurality of homopolymer tracts represents a nucleotide corresponding to a unit of data; and converting the digitized piece of data to a readable format. Steps of the method may include displaying the readable format. The plurality of homopolymer tracts may include between about 2 and about 10 nucleotide repeats. The nucleic acid memory strand may be between at least about 200 nucleotides and about 5,000 nucleotides in length.

In various embodiments, the sequencing step can comprise nanopore sequencing, sequencing by synthesis, or mass spectrometry. The sequencing, translating, and converting steps may be repeated one or more times on the nucleic acid memory strand.

Other aspects of the invention are apparent to the skilled artisan upon consideration of the following figures and detailed description.

BRIEF DESCRIPTION OF THE DRAWINGS

FIG. 4 shows the relationship of strands/GB to homopolymer length and strand length.

DETAILED DESCRIPTION

The invention provides systems and methods for writing data to and reading data from nucleic acids having homopolymer tracts corresponding to units of digital data. By repeating (e.g., 3-10 times) each nucleotide in the data-encoding sequence, only the transition between homopolymer tracts needs to be observed in sequencing reads allowing for lower fidelity, higher throughput sequencing techniques that can result in cheaper execution in nucleic acid data storage. Advantages of synthesizing nucleic acid homopolymer tract memory strands are: 1) the ability to make very long (5-10 kb) strands, which enables the use of high throughput, long read DNA sequencing technologies for readout, 2) the ability to tolerate errors in sequencing readout technologies and 3) the ability to make nucleic acid memory strands with costs far less than that of conventional chemical synthesis methods. The use of homopolymer nucleic acid memory strands is best realized in long (e.g., 5-10 kb) strands that can be efficiently produced using template-independent TdT enzymes or polymerase theta wherein homopolymer tract length can be controlled by altering exposure time and dNTP to polynucleotide memory strand ratio.

Figure 1:
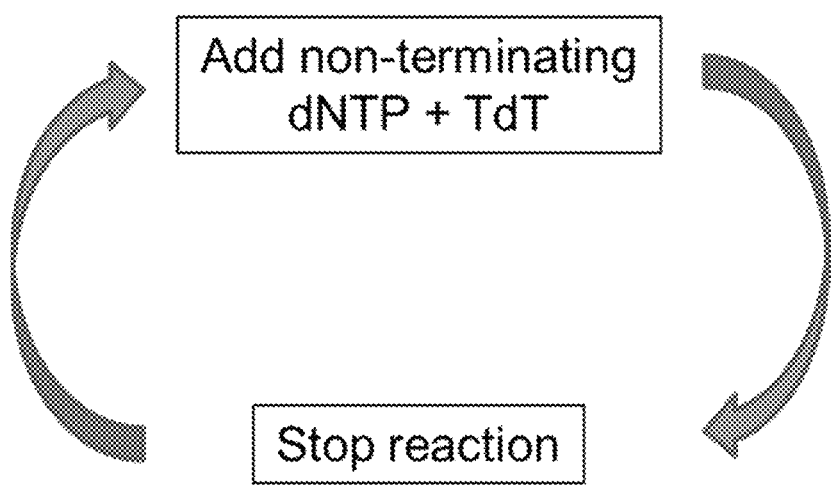
FIG. 1 shows an enzymatic synthesis cycle used to form homopolymer tracts.

The synthesis of homopolymers for encoding data by an enzymatically mediated approach is easily achieved by using natural or modified nucleotide triphosphates that are not terminators, resulting in the simplest and most rapid method of DNA synthesis possible. One natural or modified nucleotide triphosphate is delivered to a reaction zone with a nucleotidyl transferase, allowed to react and then removed by washing with a buffer thus completing one "write" cycle of data storage as illustrated in FIG. 1. The data strand synthesis occurs in entirely aqueous environment, with no toxic or hazardous chemicals, thus enabling practical devices suitable for large scale data storage centers.

Figure 2:
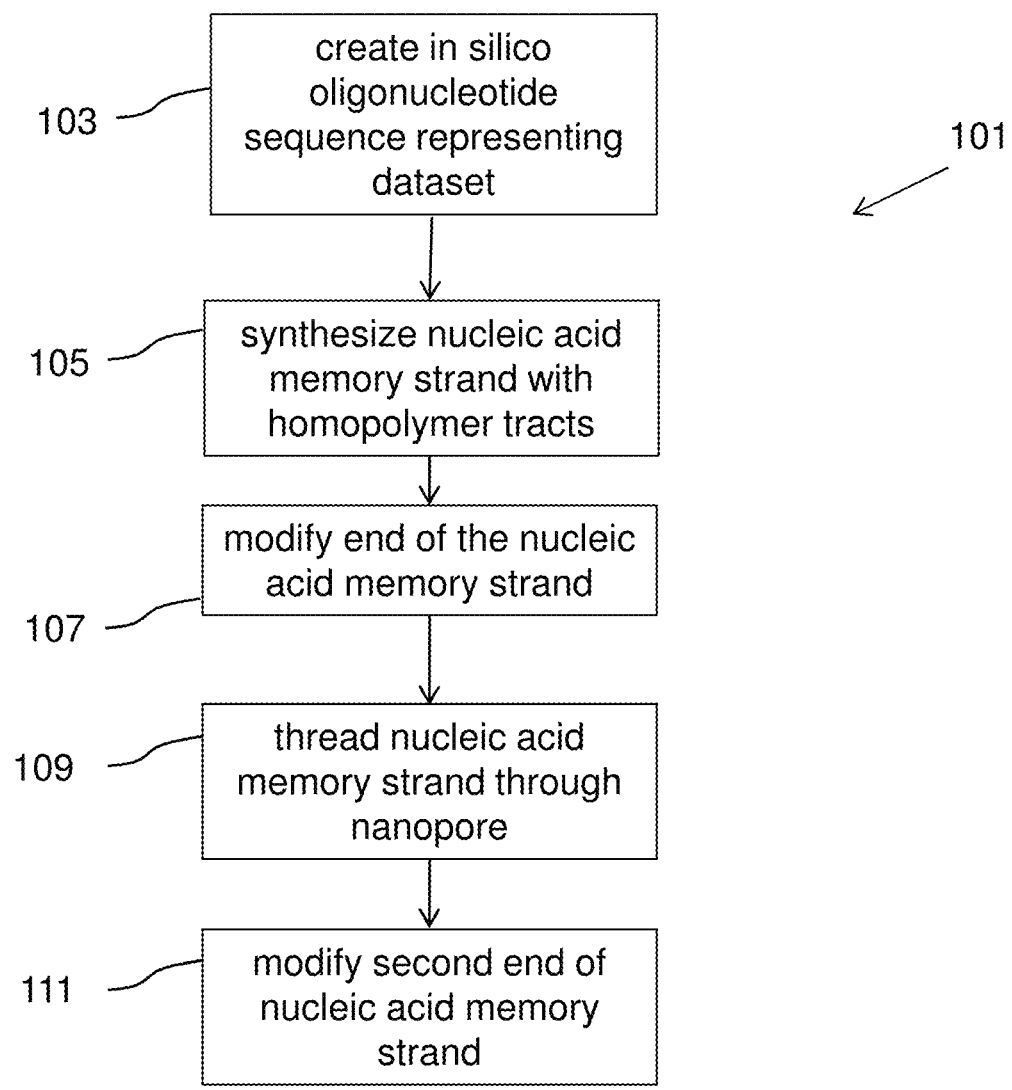
FIG. 2 shows a method of synthesizing a nucleic acid memory strand with homopolymer tracts.

FIG. 2 shows a method 101 of synthesizing a nucleic acid memory strand with homopolymer tracts according to certain embodiments. The method 101 includes creating 103 an in-silico oligonucleotide sequence representing a dataset. The dataset may comprise digitized data that may represent text, an image, a video, an audio, or any other piece of information that may be digitized. The oligonucleotide sequence may comprise any number of natural or modified nucleotides or analogs thereof and may encode the dataset using a base 2, base 3, base 4, or greater scheme depending on the number of unique nucleotides or analogs used in the memory strand. In a simple embodiment, the encoding scheme may correspond to a binary data scheme conventionally represented by a series of 0s and 1s where one or more nucleotides or analogs may correspond to 0s and one or more other nucleotides may correspond to 1s. A nucleic acid memory strand (e.g., RNA, single-stranded, or double-stranded DNA) comprising a series of homopolymer tracts each corresponding to a nucleotide, in order, in the in silico oligonucleotide sequence can then be synthesized 105. In certain embodiments, further steps include modifying 107 one end of the memory strand, threading 109 the memory strand through a nanopore and modifying 111 the other end of the strand to prevent the ends from passing through the nanopore.

Figure 3:
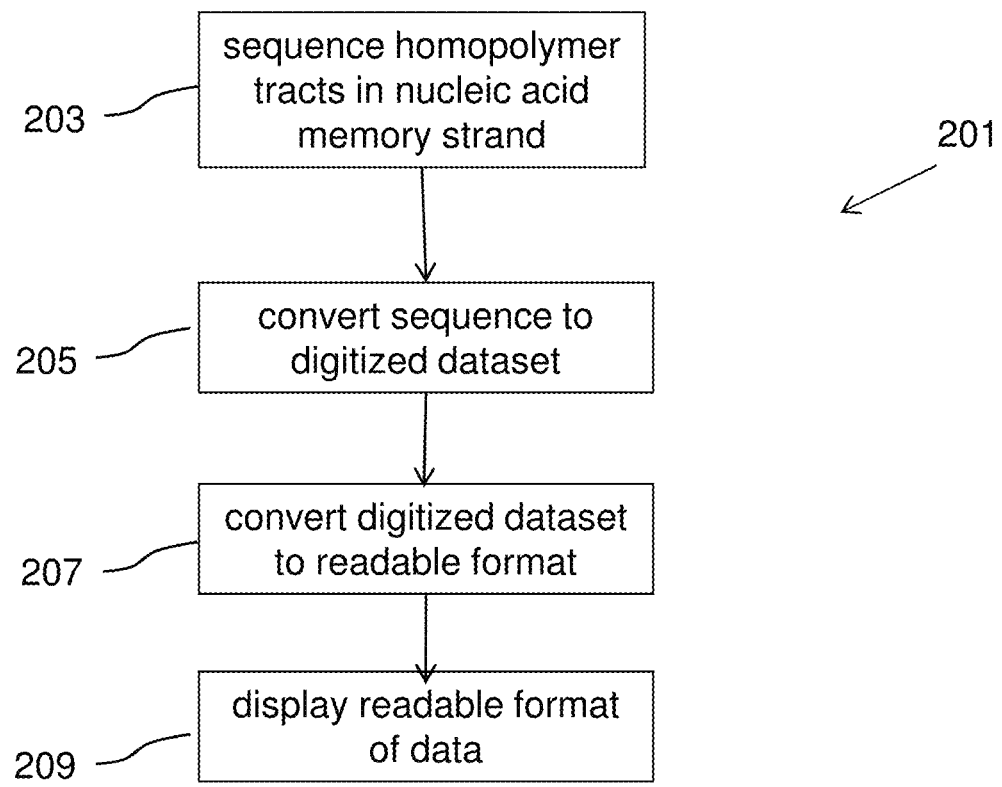
FIG. 3 shows a method of reading data from a nucleic acid memory strand with homopolymer tracts.

FIG. 3 shows a method 203 of reading data from a nucleic acid memory strand with homopolymer tracts. Steps of the method 203 include sequencing 203 a series of homopolymer tracts in a nucleic acid memory strand, converting 205 the sequence to a dataset, converting the dataset into a readable format (e.g., an image, a video, an audio clip, or a piece of text), and optionally displaying 209 that readable format of data (e.g., on a monitor or using a printer or other input/output device).

Preferably, systems and methods of the invention use long strands of DNA (5-10 kb) that are either single stranded or double stranded and may be naturally occurring or generated by chemical or enzymatic synthesis. In certain embodiments, the nucleic acid memory strands may be generated enzymatically using TdT to create a series of homopolymer tracts that may be 2-10, 3-10, 4-10 nucleotides or longer. The homopolymer tracts can each consist of Adenine (A), Guanine (G), Cytosine (C), or Thymine (T). The sequence of alternating homopolymer tracts can be used to encode the data that is to be stored in the memory strand.

Each nucleotide homopolymer tract can represent various amounts of data depending on the number of bases used. The number of bits required to make one byte (decimal 256) is defined by the following relationship: #bits/byte=8/(log 2(n)), where n=the numerical base that is used. Each tract can correspond to one bit if two base encoding is used or ¼ of a byte if four base encoding is used. In certain embodiments, DNA data strands may be composed of 2-10 nucleotide homopolymer tracts (using a base 2 dataset representation), which would allow 333 bits to 100 bits to be represented in a memory strand between 999 and 1000 bases long. In preferred embodiments, nucleic acid base encoding of data may be such that single homopolymer tracts of one nucleotide are always adjacent to homopolymer tract of a different nucleotide. For example, encoding may be such that a homopolymer tract of Adenine would not be immediately preceded or followed by another Adenine homopolymer tract. In the case where two adjacent homopolymer tracts comprise the same nucleotide, a homopolymer tract may be synthesized that is measurably longer than the average homopolymer tracts representing single nucleotides in the encoded data sequence. Those longer tracts may be created through manipulation of the synthesis reactions described below by, for example, increasing the concentration of dNTPs in the reaction or increasing the reaction time. The exact length of two adjacent identical homopolymer tracts need only be long enough to be unambiguously distinguished from single homopolymer tracts using the readout device (i.e., nanopore sequencer). In certain embodiments, a non-nucleotide homopolymer spacer could be added between A, G, C, or T homopolymer tracts to clearly distinguish adjacent same nucleotide homopolymer tracts from one another. The use of A, G, C, & T homopolymer tracts enables the creation of a four (4) bit encoding space increasing the density of data that can be stored in one contiguous strand rather than simply using two nucleotides (similar to 0s and is in binary code). For example, four contiguous homopolymer tracts can encode 256 digits (i.e., one byte) if A, G, C, & T are used in a base 4 scheme. In such an embodiment, there would be 83 bytes or 25 bytes represented in a 996 or 1000 nucleotide long nucleic acid memory strand if three (3) nucleotide long homopolymer tracts or ten (10) nucleotide long homopolymer tracts were used respectively.

In various embodiments, base 8 or even base 12 coding schemes may be employed through the incorporation into the memory strand of homopolymer tracts of uniquely modified nucleotide or non-nucleotide analogs. Those modified nucleotide or non-nucleotide analogs should generate a unique digital signal with a readout device like a nanopore sequencer or a single molecule ZMW sequencer. TdT, as discussed below, can incorporate a wide range of modified dNTP analogs that can enhance the signal provided by a readout device like a nanopore and thus may be used for generating nucleic acid memory strands with data encoded in them. Homopolymers of modified nucleotides (e.g., A*, G*, C* & T* or A, G, C & T) can be synthesized using TdT and modified dNTP analogs (e.g., dA*TP or dA**TP) of each of the four bases to generate an eight (8) bit or even a twelve (12) bit encoding scheme. Higher base (n) encoding allows for data compression and results in a reduction in the number of DNA strands that are required to encode a given amount of information. The relationship determining the number of DNA strands per GB of data as a function of the length of the homopolymer tract, the numerical base (n), and the strand length synthesized is defined by: #strands/GB=(8/(log 2(n))*$10^9$*homopolymer length*1/strand length as illustrated in FIG. 4.

The number of unique homopolymer tracts may be limited only by the ability of the readout technology (i.e., nanopore or ZMW single molecule sequencing) to determine one homopolymer tract from another. There are several reports in the literature of the detection of homopolymers composed of unmodified nucleotides by detecting the change in the ionic current during translocation through nanopores (Venta et al, 2013; Feng et al, 2015). Modifications that alter the dwell time of the DNA in the nanopore will generate a distinguishable and characteristic ionic-current signal. Singer et al 2010 and Morin et al 2016 use non-covalently bound bisPNA or γPNA functionalized with 5 or 10 kDa PEG to enhance detection by nanopores. Liu et al 2015 selectively created adamantly 8-oxoG analogs to modify the dwell time and generate a unique signal. Given the tolerance of TdT to incorporating bulky modifications at N6 of dATP, N4 of dCTP, N2 or O6 of dGTP and O4 or N3 of dTTP, acyl or alky modifications at those positions may be screened and chosen to enhance the detection modality of nanopore or ZMW single molecule sequencing technologies. Detection may be improved through modified nucleotides that enhance the differential current blockade in a nanopore or enhance the dwell time of a modified nucleotide in the active site of a DNA polymerase in a ZMW single molecule approach. Other natural and non-natural purine and pyrimidine nucleotide analogs may be used if they generate a unique digital signal with a readout device like a nanopore sequencer or a single molecule ZMW sequencer. Modifications at the C5 or C7 of pyrimidines and purines respectively may be used if they generate a unique digital signal with a readout device like a nanopore sequencer or a single molecule ZMW sequencer. Suitable modified nucleotide triphosphates are chosen to be rapidly incorporated during the enzymatic extension step and provide a substitution-specific dwell time with as short of a homopolymer as possible during the detection step. Examples of modifications to A, G, C, & T bases suitable for expanding the bit encoding space may include but are not limited to N6-benzoyl dA, N6-benzyl dA, N6-alkyl dA, N6-acyl dA, N6-substituted alkyl dA, N6-substituted acyl dA, N6-aryl acyl dA, N6-substituted aryl acyl dA, N2-alkyl-dG, N2-acyl dG, N2-aryl acyl dG, N2-substituted alkyl dG, N2-substituted acyl dG, N2-substituted aryl acyl dG, 6 alkyl dG, O4 alkyl dT, N3 alkyl dT, N3 acyl dT, O6 substituted alkyl dG, O4 substituted alkyl dT, C5-propargyl amine dT, C5-propargyl amine dC, C7-propargyl amine dA, C7-propargyl amine dG, substituted C5-propargyl amine dT, substituted C5-propargyl amine dC, substituted C7-propargyl amine dA, substituted C7-propargyl amine dG. Preferred embodiments of substitutions include but are not limited to covalent attachments that are completely stable to removal except under the most extreme chemical conditions of pH, temperature and concentration of reactive species. Substitutions that are able to affect a unique current blockade may include but are not limited to alkyl, heteroatom substituted alkyl, aromatic hydrocarbons, alkyl substituted aromatic hydrocarbons, heteroatom substituted alkyl substituted aromatic hydrocarbons, heteroatom substituted aromatic hydrocarbons, benzyl, substituted benzyl or combinations of the such. In some embodiments, the substitutions can be polyethylene glycols composed of 2 to 450 monomer units. In some embodiments, substitutions comprised of peptides or peptoids may be suitable to increase the dwell time of homopolymers in a specific and discernable manner. The efficiency of incorporation of modified nucleotides by template-independent polymerases like TdT may be modulated by the use of different metal ion cofactors such as but not limited to Co++, Zn++, Mg++, Mn++, or mixtures of two or more different metal ions. Each modified nucleotide may require a different metal ion for optimal performance during enzymatic homopolymer synthesis.

Since long term stability of the DNA data strands is essential, there is a distinct advantage to using non-purine based homopolymers since they are subject to depurination at low pH. In some embodiments, the homopolymer bits can be composed of only a single nucleotide type (i.e., Thymine) that is modified with two, three, four or more different chemical groups resulting in homopolymer tracts that each result in a unique current blockade. Thus, one nucleotide labeled with four unique modifiers can substitute for the presence of A, G, C, T. Other embodiments that use only one of the other three nucleotides with two, three, four or more different chemical groups are possible.

If the modified nucleotide analogs are sufficient enough to cause a unique dwell time for the passage of a single nucleotide through a nanopore, another embodiment would use single nucleotide bits instead of homopolymer bits. Single modified nucleotide bits would be advantageous in allowing the maximum density of information per DNA strand thus reducing the cost of DNA based data storage.

The precise length of the homopolymer tract is not critical so long as the sequencing technology used for the read-out can clearly distinguish the start and stop of one homopolymer tract from another. Although there are distinct synthesis and storage density advantages to increasing the number of unique nucleotides or bases (including modified nucleotide or non-nucleotide analogs) used and therefore reducing the length needed to capture a set amount of data, the lowest cost per DNA data storage synthesis may be achieved by using four natural nucleotide dNTP monomers during enzymatic synthesis since those reagents are widely used in the molecular biology & sequencing fields and are produced in very large batches with the lowest manufacturing cost. The cost of production of dNTP analogs to increase the number of unique homopolymer tracts may be reduced as the use of DNA data storage increases and manufacturing scale of analogs is also increased.

Any method of synthesizing the homopolymer tract segment may be used with systems and methods of the invention but preferred embodiments use the template-independent enzyme TdT. TdT provides certain benefits insofar as it will rapidly and inexpensively generate a homopolymer with a Poisson distribution where the average size of the homopolymer may be strictly controlled by the ratio of the [dNTP] to the nascent oligonucleotide memory strand. In some embodiments, polymerase theta in the presence of $Mn^{2+}$ can be used as a template-independent polymerase to synthesize homopolymer tract nucleic acid memory strands. In another embodiment, the length of the homopolymer tract segments can be controlled by delivering an excess of dNTP to a reaction zone and then removing the reactants after carefully controlled interval of time.

TdT has demonstrated the ability to synthesize homopolymer tracts of a fairly defined length by controlling the ratio of dNTP concentration to the concentration of 3'-ends of the nucleic acid strand desired to be modified. Inkjet synthesis on array-based formats is capable of very low cost phosphoramidite synthesis but the strands that are made are limited to 100-200 bases in length, must sacrifice some of the length to index sequences, are made in sub-femtomolar scale requiring post-synthesis amplification to provide sufficient material for subsequent read-out and are mostly suited for relatively inefficient short read sequencing readout technologies.

Strands of single stranded DNA synthesized according to processes of the invention may benefit from the prevention of hairpins or dsDNA either during the synthesis or during the readout. Hairpin formation can be prevented by modifying the exocyclic amines of one member of a A:T or G:C base pair to prevent the hydrogen bonding necessary for base pairing. In some embodiments, the exocyclic amines may be modified by acylation or alkylation. Any simple and stable modification of the exocyclic amines of A, G or C, which prevents base pairing can be used to prevent hairpin formation. In certain embodiments, the N6 of deoxyadenosine and the N2 of deoxyguanosine may be acetylated with an acetyl group preventing base pairing. In some embodiments, the N6 of deoxyadenosine and the N4 of deoxycytidine can be modified to prevent base pairing and hairpin formation. In some embodiments, the O6 of deoxyguanosine or the 6 of deoxythymidine can be modified to prevent base pairing and hairpin formation. In some embodiments, the O4 of deoxythymidine or the N3 of deoxythymidine can be modified to prevent base pairing and hairpin formation. In some embodiments, modifications to A, G, C, or T to generate higher order base encoding schemes also serve the purpose of preventing base pairing and hairpin formation. In some embodiments, homopolymer bits can be composed of only a single nucleotide type (i.e., Thymine) that is modified with two, three, four or more different chemical groups that result in a unique current blockade and prevent the formation of intra- or inter-strand double strand regions. In another embodiment, a thermostable version of TdT or another template-independent nucleotidyl transferase can be used to perform strand synthesis at an elevated temperature, thus preventing prevent the formation of intra- or inter-strand double strand regions.

Control of the homopolymer tract length can be optimized for any analogs as described above after determination and calibration of the incorporation rate of the dNTP analog to create a reproducible range of homopolymer tract lengths of 2-10 nucleotides in length. The use of A*, G*, C*, & T* and A, G, C & T homopolymer tracts allows the creation of an eight (8) bit or twelve (12) bit encoding, increasing the density of data that can be stored in one contiguous strand rather than simply using two nucleotides to encode for a "0" and a "1". Three (3) contiguous homopolymer tracts can encode 256 digits (i.e., one byte) if A, G, C, T, A*, G*, C*, & T* are used. In such embodiments, there would be 111 bytes or 33 bytes in a 999 or 990 nucleotide long nucleic acid memory strand if three (3) nucleotide long homopolymer tracts or ten (10) nucleotide long homopolymer tracts were used respectively. Two (2) contiguous homopolymer tracts can encode 256 digits (i.e., one byte) if A, G, C, T, A*, G*, C*, T*, A, G, C, & Tare used. In those embodiments, there would be 166 bytes or 50 bytes in a 996 or 1000 nucleotide long nucleic acid memory strand if three (3) nucleotide long homopolymer tracts or ten (10) nucleotide long homopolymer tracts were used respectively.

Figure 5:
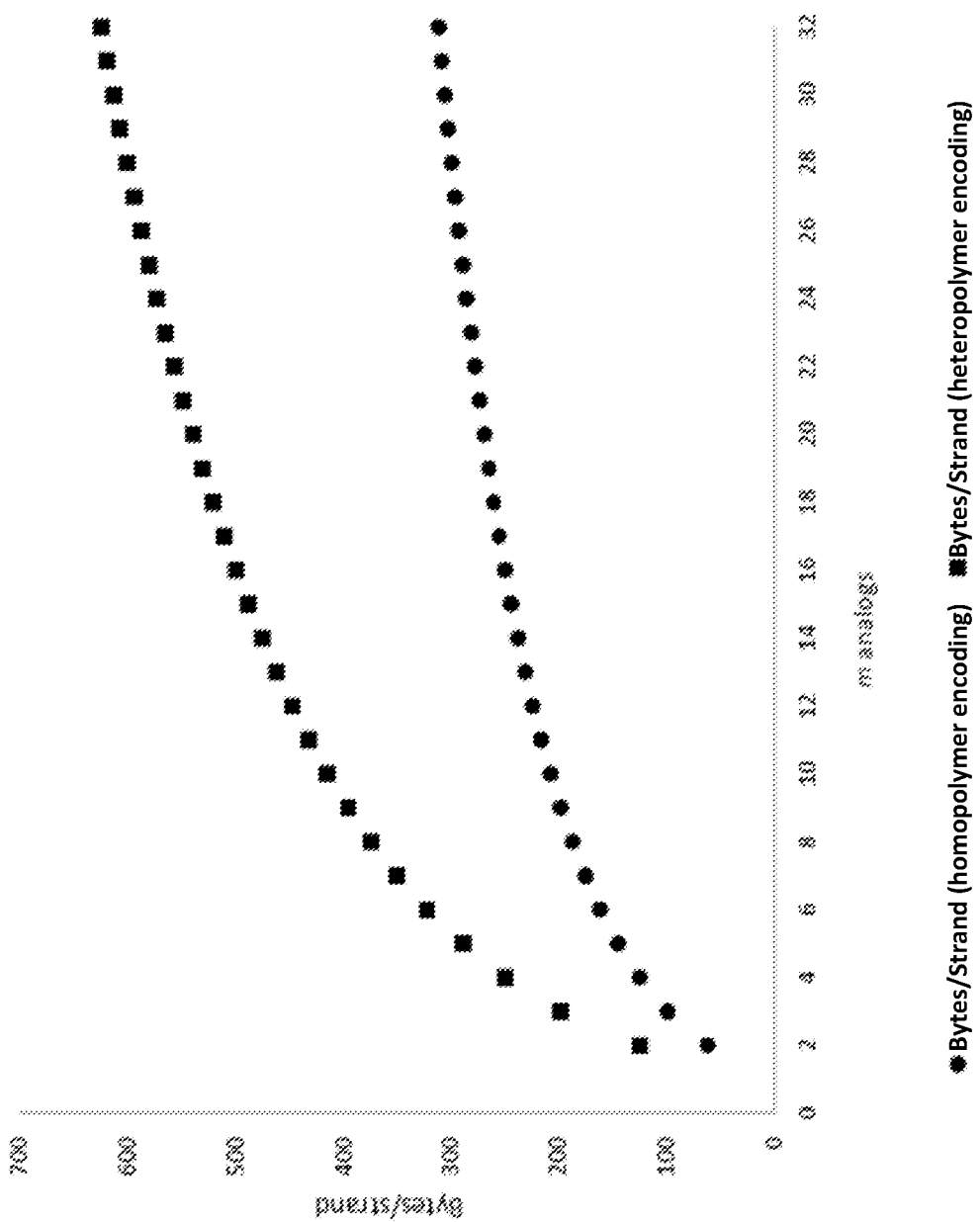
FIG. 5 shows the data that can be encoded in a DNA strand comprised of 500 polymer tracts as a function of the number of distinguishable nucleotide analogs in a memory strand.

In certain embodiments, data may also be encoded in the memory strand heteropolymer tracts of random sequence and defined composition to achieve a higher level of data compression. The heteropolymer stretches can be generated with enzymatic reactions using mixtures of different dNTPs, where the dNTP stoichiometry is used to control the composition of the heteropolymer tracts. The number and type of heteropolymer tracts is limited only by the combinations of dNTP analogs and the ability of the detection modality to distinguish the compositions of the different tracts. For m dNTP analogs, there are $(m^2-m)/2$ binary combinations for heteropolymer formation. Detection modalities which can distinguish two different levels of tract compositions for each binary combination (e.g. a tract where analogs A and B are present in an approximately 2:1 ratio respectively and a tract where they are present in a 1:2 ratio) allow data to be encoded at a rate of base $m^2$ from a set of m analogs, effectively doubling the coding capacity of the memory strands. FIG. 5 illustrates the data that can be stored in a memory strand as a function of the number of available dNTP analogs using either homopolymer and a binary heteropolymer-based encoding scheme with two levels tract composition.

Data encoding strands of the invention may not necessarily require precisely defined homopolymer lengths since they only need to be long enough (ca 2-10 nucleotides) to allow the unambiguous discrimination of the transition between homopolymer tract segments by a high throughput DNA sequencing technology. Existing Nest Generation Sequencing-by-Synthesis (SBS) systems can readily determine the transition between two adjacent homopolymer tracts. Again, the precise length of the homopolymer tract is not important to the accurate detection of a homopolymer bit. The use of tracts of the same nucleotide offers advantages in overcoming the most common errors in current SBS platforms: insertions and deletions. The deletion of one nucleotide in a homopolymer tract >2 nt will still be interpreted as a true homopolymer. Likewise, the insertion of a single nucleotide in a homopolymer tract would not be falsely interpreted as two adjacent homopolymers since the insertion of more than one nucleotide during SBS is an unlikely event. This sequencing error tolerance offers the advantage of decreasing the sequencing depth required to ensure correct decoding of the information stored by the DNA data strand. Existing nanopore systems can easily distinguish homopolymer tracts of A, G, C, or T from each other based on their differential current blockade. In certain embodiments, single molecule ZMW sequencing can be used to determine the linear order of homopolymer tracts on a linear strand. The use of either sequencing technology may require that the DNA initiator has properties that are compatible with the sequencing readout technology like a self-complimentary hairpin at the 5'-end of a synthesized single stranded memory strand to provide a primer for single molecule ZMW sequencing. Nanopore sequencing technology may also require a self-complimentary hairpin at the 5'-end of the strand to provide a "start" data mark. In various embodiments, the readout technology may be any next generation sequencing method such as that offered by Illumina (San Diego, Calif.). In some embodiments, the readout or sequencing technology may be Mass Spectrometry based. The technology specific error rate of the readout technology is not important so long as it can unambiguously detect the transition between two different homopolymer tract and/or unambiguously detect the difference between one homopolymer tract length and one 2× in length in the case where two identical homopolymer tracts are adjacent to each other.

Certain read-out technologies may be preferable to others based on the specific application of the invention. Technologies such as nanopore sequencing can be non-destructive and leave the nucleic acid memory strand intact, suitable for multiple read-out cycles. Read-out technologies that are dependent on Sequencing by Synthesis (SBS) like ZMW single molecule and others, generate a copy of the original template strand and may require post-readout manipulation (i.e., strand separation by melting) to remove the complimentary strand and return the original nucleic acid memory strand to its pristine state ready for a subsequent cycle of readout. Other readout technologies, like mass spectrometry, are destructive and would deplete the pool of nucleic acid memory strands after repeated cycles of sampling and readout.

In various embodiments nucleic acid memory strands may include "stoppers". "Stoppers" may be macromolecular constructs which prevent the passage of a single stranded or double stranded nucleic acid through a nanopore (Manrao, et al., 2012, Reading DNA at single-nucleotide resolution with a mutant MspA nanopore and phi29 DNA polymerase, Nature Biotechnology 30, 349-353, incorporated herein by reference). Proteins like phi29 DNA polymerase are large enough to not be drawn through the larger pore (about 6.3 nm) on the cis side of a protein nanopore. The pore diameter of the smaller side is estimated to be about 1.2 nm wide. Stoppers can be used either on the 5'- or 3'-end of a nucleic acid memory strand of the invention. In some applications, it may be desirable to have a stopper at both the 3'- or 5'-end of a nucleic acid molecule. Stoppers can consist of a hairpin (stem-loop) structure with either a protruding 5'- or 3'-overhang to which the information encoding nucleic acid is covalently attached. If the stopper consists of a hairpin, the length of the ds stem may be sufficiently long to resist any melting force exerted on it by the electric field used to translocate the memory strand through the nanopore. In certain embodiments, one base of the double-stranded stem region can be crosslinked to its cognate base that forms that base-pair so that it is impossible for the double-stranded stem portion of the hairpin to melt under the influence of the force exerted on it by the electric field that translocates the rest of the molecule through a nanopore. To utilize a hairpin stopper for TdT mediated nucleic acid memory synthesis according to certain embodiments, the stopper may have a 3'-overhang of sufficient length (i.e., >10 nucleotides) to allow the binding of TdT for template independent synthesis.

Stoppers may consist of a non-nucleotide macromolecular construct which can be appended to either the 3'- or 5' end of a nucleic acid molecule. The construct can be synthesized by direct conjugation of a macromolecular species onto the 3'-end of a nucleic acid by a polymerase or transferase like TdT (Sorensen, et al., 2013, Enzymatic Ligation of Large Biomolecules to DNA, ACS Nano, 7(9):8098-8104, incorporated herein by reference) or by the incorporation of a functionalized nucleotide which allows the specific modification of the nucleic acid via that functionality (Winz, et al., 2015, Nucleotidyl transferase assisted DNA labeling with different click chemistries, Nucleic Acids Res. 43(17):e110, incorporated herein by reference). 5'-end stoppers may be readily introduced at the time of chemical synthesis of an oligonucleotide adapter either via direct synthesis of a hairpin or via secondary modification of a functional handle introduced as the last step of the 3' to 5' oligonucleotide synthesis and may be used as an initiator. Alternatively, 5'-end stoppers can be constructed by attaching an oligonucleotide initiator via the 5'-end to a magnetic or non-magnetic bead or particle or nanoparticle, enzymatically synthesizing the homopolymer tract containing memory strand and then leaving the memory strand attached to the magnetic or non-magnetic bead or particle or nanoparticle.

Stoppers can be further modified to allow cleavage of the stopper from the rest of the molecule to allow the nucleic acid strand to either passively diffuse out of the nanopore or to be translocated out of the nanopore through the application of a voltage thus allowing strand to be recovered.

In certain embodiments, template independent polymerases or transferases can be used to modify pre-synthesized strands of nucleic acids to enable the use of nanopore devices as "Write Once, Read Many" types of memory devices. Part of the inherent issues associated with the use of nanopore devices as DNA sequencers is the high error rate they produce because of the poor discrimination of the nanopore. This may be due to the speed of translocation through the pore or the fact that the approximate depth of the nanopore is 8 nm, allowing for multiple bases to be present in the pore at the same time. The homopolymer memory strands of the invention address this issue through the use of homopolymer repeats, decreasing the need for strict sequencing accuracy. In certain embodiments, the shortcomings of nanopore sequencing may be addressed by implementing a hairpin adapter to one end of a double stranded DNA memory strand such that during the translocation and base calling process, each sense of the DNA memory strand could be read such that reading an individual base and its complementary strand could compensate for the error rate of reading each base only once. In certain embodiments, nanopore sequencing fidelity may be increased by appropriate modification of each end (5'-& 3'-) of a single-stranded or double-stranded nucleic acid molecule with a bulky appendage that will not translocate across a pore (e.g., protein or solid state). The molecule may then be trapped within a pore and translocated forwards and backwards many times to allow multiple reads of the same molecule in the same pore thus reducing the sequencing error rate by the square of the number of reads (if the sequencing read errors are due to stochastic origins).

Transferases like TdT may be used to append large and bulky modified nucleotide analogs to the 3'-end of a DNA molecule. In certain embodiments, a WORM nanopore memory device may be generated using the following steps: (1) generating a single molecule of DNA encoding specific information in any high density encoding scheme as discussed above and covalently modifying the 5'-end with a bulky molecular construct that prevents complete translocation of the DNA molecule through a nanopore; (2) threading the DNA molecule through the nanopore until the 5'-modified end is in contact with the nanopore and it cannot translocate any further; (3) using TdT and a modified nucleotide to covalently add one (or more) bulky nucleotide analogs ("stoppers") to the 3-end of the DNA molecule to effectively trap the molecule within the torus of the nanopore; (4) reversing the polarity of the current to the nanopores to clear out any DNA molecules that are not 3'-modified thus creating a pure population of "trapped" (5'-& 3'-modified) nucleic acid strands; (5) removing any un-trapped nucleic acids from the vicinity of the nanopore through washing or other means; (6) reading the "trapped" DNA strand in either or both directions, using an applied voltage, (potentially reading multiple times to reduce the error rate to an acceptable level). In various embodiments, step 6 may consist of a voltage induced "read" in one direction, and rapid translocation in the opposite direction to "rewind" the data encoding nucleic acid through the nanopore followed by another voltage induced "read" in the original direction. This cycle of "read"-"rewind"-"read" can be repeated as many times as desired.

In some embodiments, the trapped nucleic acid strand may be read during translocation in either direction. In some embodiments, the trapped strand can be translocated to one end of the molecule (either 5'- or 3'-) and read in the opposite direction as such a polarity of reading may provide a higher accuracy read.

Figure 6:
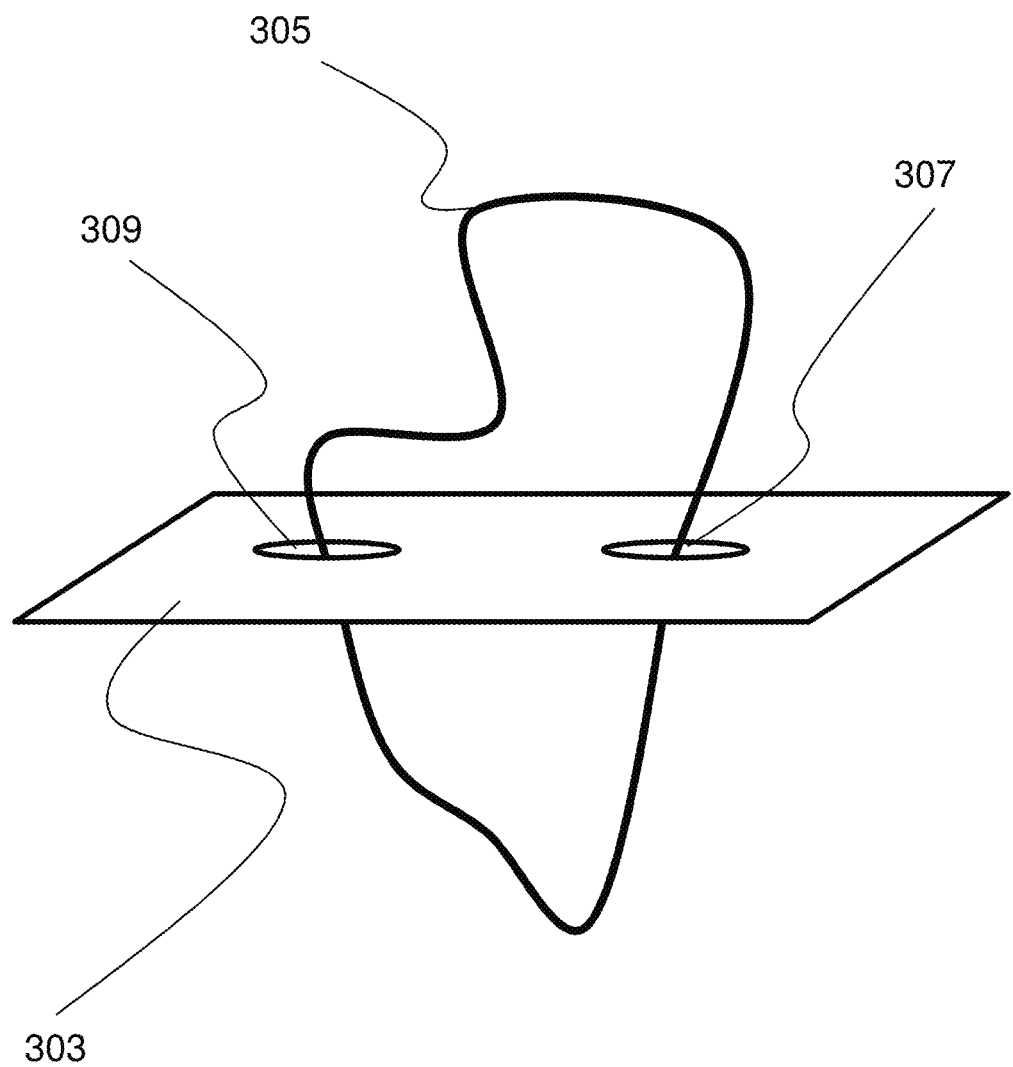
FIG. 6 shows a nanopore trapped nucleic acid memory strand of the invention.

In certain embodiments, a circularized nucleic acid memory strand may be generated using synthesis methods described above followed by circularization. The circularized strand may comprise a bulky macromolecule or specific homopolymer sequence where the ends of the synthesized strand were joined in order to designate a start and stop point for data reading. Start and stop homopolymer sequences may also be used in linear nucleic acid strands. The circularized strand 305 may have been threaded between two adjacent nanopores (306 and 309) such that the circular strand 305 is physically trapped between the two nanopores (306 and 309) located on a single membrane 303 as shown in FIG. 6. The circularized memory strand may encode digital information as either sequences of single nucleotides, homopolymer tract sequences, sequences of modified nucleotide analogs, or some combination thereof. One nanopore 309 may be used to generate an electrical signal as the information-encoded memory strand is translocated though the pore, while the other nanopore 307 may simply act as a portal to allow the DNA molecule to return to the cis side of membrane 303 and first nanopore 309. One advantage of this scheme is that the information encoding strand may be recycled for repeated reading and can be read multiple times to thus reduce any possible read-out error.

Figure 7:
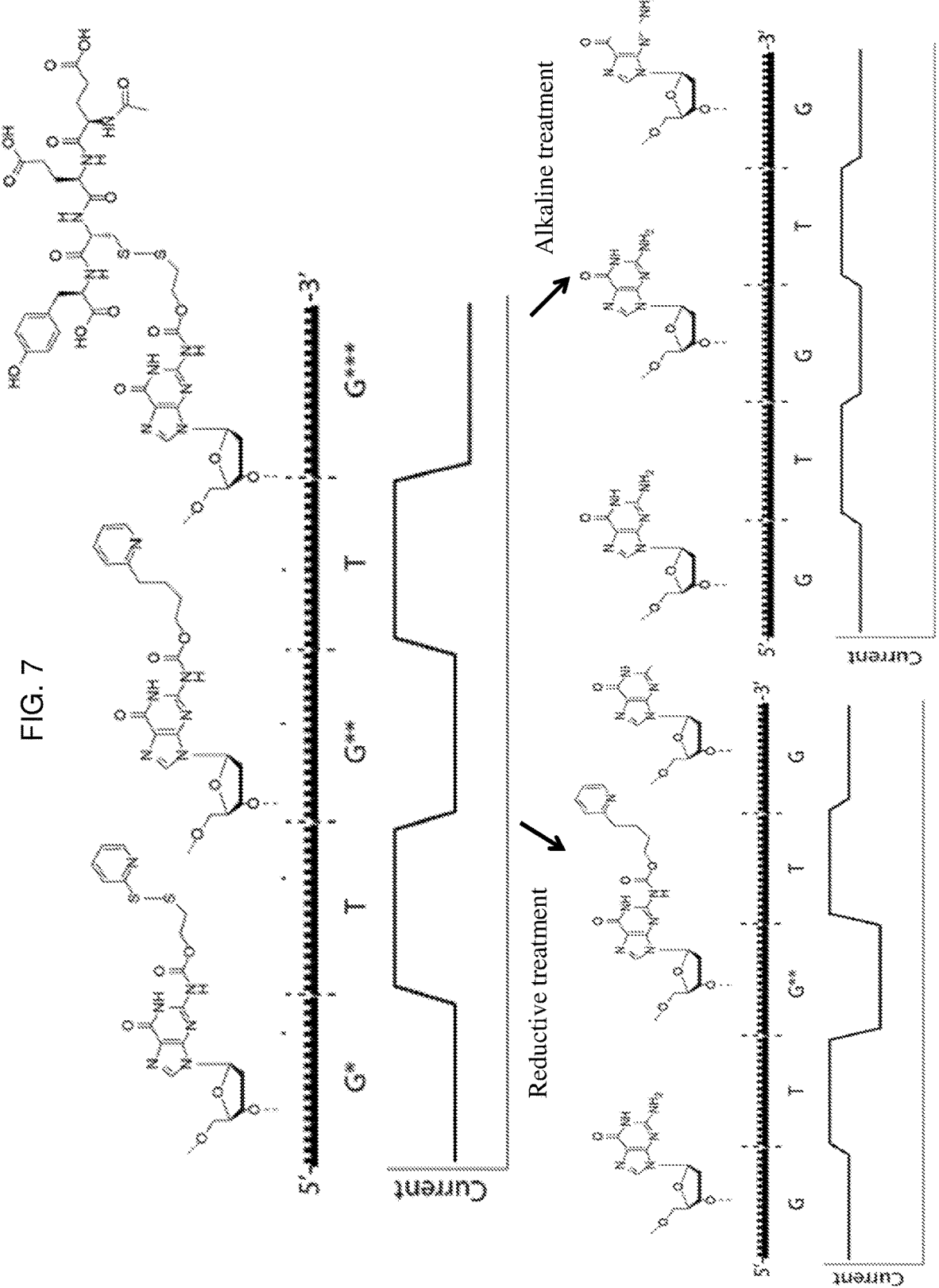
FIG. 7 shows a scheme for changing the data encoded within a strand of homopolymer tracts in response to treatment conditions.

Other embodiments may encode data in the memory strands so that it can be accessed only under a specific set of conditions. In such cases the memory strands are at least partially comprised of nucleotides containing modifications attached with a cleavable linker. Modifications (e.g., chemical protecting groups) and linkers can be selected so that if a polymer tract translocates through a nanopore without the correct treatment, the current blockades differ from the sequence that encodes the data. FIG. 7 outlines a scheme using disulfide and amide-linked modifications to a dG nucleotide and illustrates how the current blockade and data encoded in the memory strand may change in response to treatment conditions. G* and G** are structurally similar in size and flexibility and may produce similar current blockades on nanopore platforms, yet are removed under different conditions. G* and G*** are structurally different yet the modifications share the same removal conditions. Other embodiments may employ other modifications or linkers that are cleavable with different treatments such as specific wavelengths of light, acidic or alkaline pH, oxidative or reductive conditions, or sequence-specific nucleases. Some embodiments may use the presence or absence of memory strand modifications for encryption or as a chemical marker of previous access or alteration to the data. Most linker cleavage reactions are effectively irreversible, so this approach is best suited for write-one read many systems where single molecules may be sufficient to encode data without redundancy.

Many possible information encoding schemes which are useful with readout schemes of the invention are possible and may be apparent to one skilled in the art based on the present disclosure.

Synthesis may be accomplished using acoustic delivery of drops into wells of plates (e.g., 1536 well plates of 1.5 µL each). In various embodiments, nucleic acid memory strands may be synthesized on a bead or a magnetic bead or a surface and either left on the bead or magnetic bead or surface after the full-length synthesis is complete or removed from the synthesis support depending on the application.

In certain embodiments, systems for the synthesis of long (5-10 kb) data strands may use inkjet delivery to arrays of wells (e.g., multiple nanoliter volume wells). In other embodiments, multiple pneumatically controlled actuators can be positioned above each well to simultaneously deliver reagents to each position of an array. Each actuator would be served by a selector valve that would choose between each of the two or more nucleotides or modified nucleotides formulated with a template-independent polymerase that are used to specify the bits of the DNA data strand. One or more additional selector valve ports would be dedicated to one or more wash reagents if necessary. The array of nanoliter volume wells can be open at both ends, as long as the diameter of the wells is such that delivered liquids are trapped by capillary action within the length of the open-ended wells. After each round of nucleotide-enzyme formulation is delivered to the open-ended well, a rinse reagent or enzymatic reaction stop reagent can be flowed across and through the lower opening of the array of wells such that each well is rinsed of the reaction mixture thus preparing the array for the next cycle of enzymatic synthesis. In other embodiments, a vacuum source is used to rapidly remove one reagent from the capillary nanowells prior to delivery of the next reagent.

Figure 8:
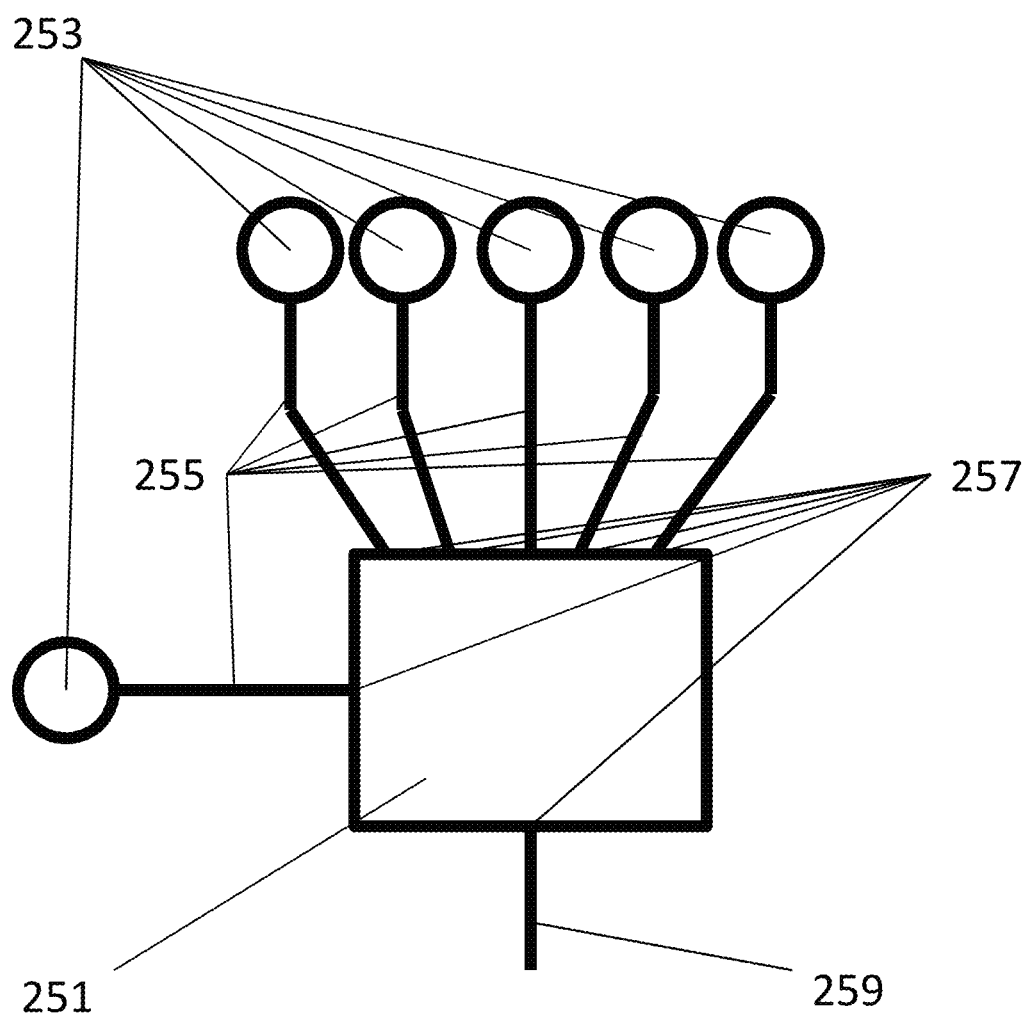
FIG. 8 shows a system for synthesizing nucleic acid memory strands with homopolymer tracts.

Certain embodiments may use highly parallel nanofluidic chambers with valve-controlled reagent deliveries. An exemplary microfluidic nucleic acid memory strand synthesis device is shown in FIG. 8 for illustrative purposes and not to scale. Microfluidic channels 255, including regulators 257, couple reservoirs 253 to a reaction chamber 251 and an outlet channel 259, including a regulator 257 to evacuate waste from the reaction chamber 251. Microfluidic devices for nucleic acid memory strand synthesis may include, for example, channels 255, reservoirs 253, and/or regulators 257. Nucleic acid memory strand synthesis may occur in a microfluidic reaction chamber 251 which may include a number of anchored synthesized nucleotide initiators which may include beads or other substrates anchored or bound to an interior surface of the reaction chamber and capable of optionally releasably bonding a polynucleotide initiator. The reaction chamber 251 may include at least one intake and one outlet channel 259 so that reagents may be added and removed to the reaction chamber 254. The reaction chamber 251 should be temperature controlled to maintain optimal and reproducible enzymatic synthesis conditions. The microfluidic device may include a reservoir 253 for each respective dNTP or analog to be used in the memory chain coding scheme. Each of these reservoirs 253 may also include an appropriate amount of TdT or any other enzyme which elongates DNA or RNA strands in a template-independent manner. Additional reservoirs 253 may contain reagents for washing or other tasks.

The reservoirs 253 can be coupled to the reaction chamber 254 via separate channels 255 and reagent flow through each channel 255 into the reaction chamber 254 may be individually regulated through the use of gates, valves, pressure regulators, or other means. Flow out of the reaction chamber 254, through the outlet channel 259, may be similarly regulated. The reservoirs 253 may hold dNTPs, modified dNTPs or any analogs thereof described above suspended in a fluid at a known concentration such that the concentration of reagent may be strictly controlled based on the volume of reagent allowed to flow into the reaction chamber 254. Accordingly, the length of each homopolymer tract may be managed through control of the reagent concentration.

In certain instances, reagents may be recycled, particularly the dNTP and enzyme reagents. Reagents may be drawn back into their respective reservoirs 253 from the reaction chamber 254 via the same channels 255 through which they entered by inducing reverse flow using gates, valves, vacuum pumps, pressure regulators or other regulators 257. Alternatively, reagents may be returned from the reaction chamber 254 to their respective reservoirs 253 via independent return channels. The microfluidic device may include a controller capable of operating the gates, valves, pressure, or other regulators 257 described above.

An exemplary microfluidic nucleic acid memory strand synthesis reaction may include flowing a desired dNTP (used throughout to refer reference any component molecule used to encode data in a nucleic acid memory chain of the invention) reagent into the reaction chamber 254 at a predetermined concentration and for a predetermined amount of time (calculated to result in the desired homopolymer length) before removing the NTP reagent from the reaction chamber 254 via an outlet channel 259 or a return channel (not shown); flowing a wash reagent into the reaction chamber 254; removing the wash reagent from the reaction chamber 254 through an outlet channel 259; flowing the next NTP reagent in the desired memory strand sequence under conditions calculated to achieve the desired homopolymer tract ratio; and repeating until the desired nucleic acid memory strand has been synthesized. After the desired nucleic acid memory strand has been synthesized, it may be released from the reaction chamber anchor or substrate and collected via an outlet channel 259 or other means.

Figure 9:
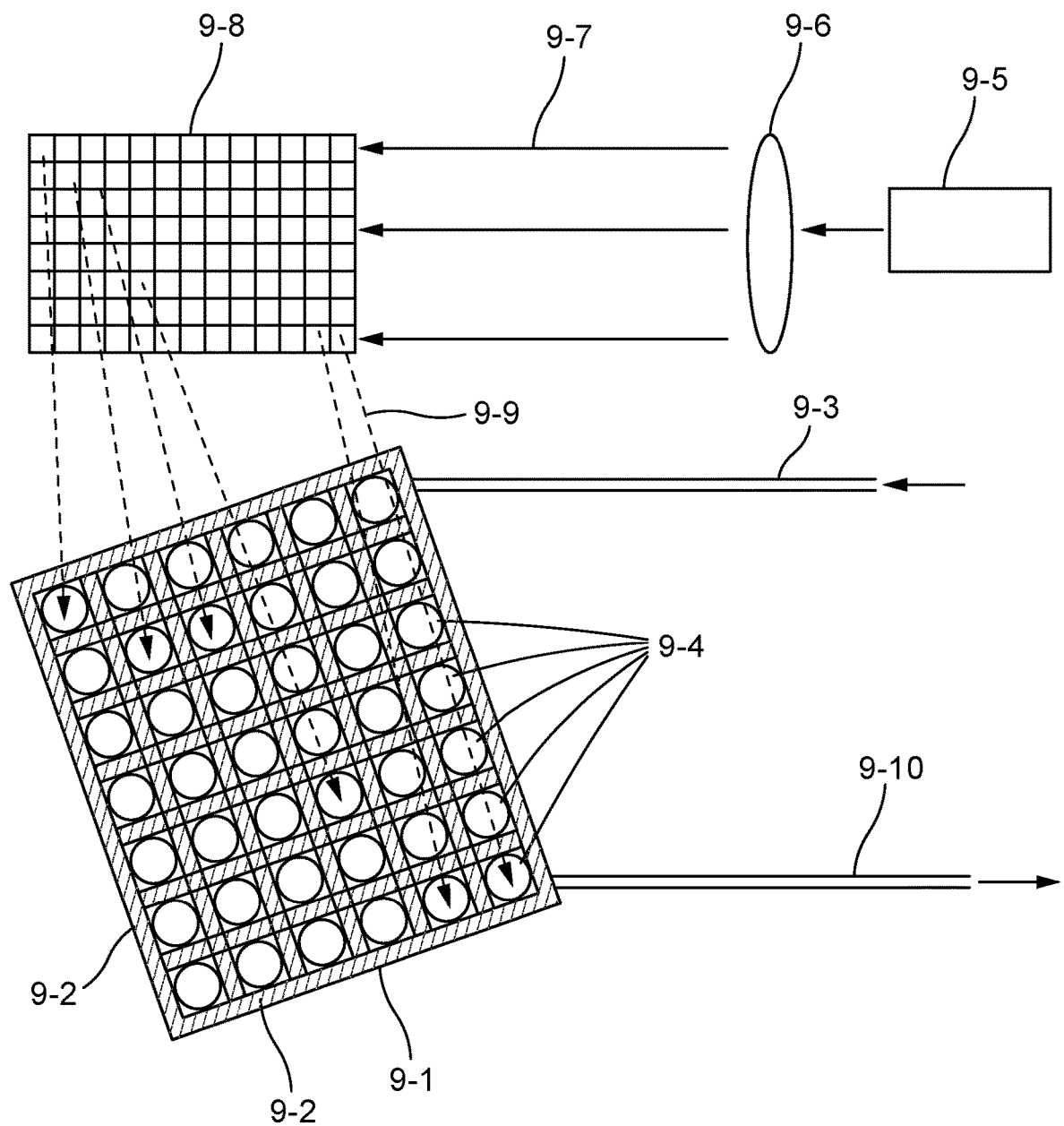
FIG. 9 shows a system for the parallel synthesis of nucleic acid memory strands with homopolymer tracts on an array of nanowells.

Because of the significant number of homopolymer encoded DNA strands required to encode useable amounts of data, highly parallel methods of DNA synthesis are required. In one embodiment, as depicted in FIG. 9, a flow cell containing an array of wells (9-1) are formed on a suitable substrate by patterning horizontal and vertical stripes (9-2) of hydrophobic materials to form a plurality of hydrophilic wells (?) bordered by hydrophobic regions. Typical dimensions of the hydrophilic wells can be 300×300 nm to 1000×1000 nm. This hydrophilic array forms the floor of a flow cell with a gap of suitable dimensions between the floor and an optically transparent cover. A solution of cold (i.e., below the enzyme-specific temperature optimum)

nucleotidyl transferase, one of natural or modified nucleotide triphosphates and any necessary co-factors, is flowed into the flow cell through an inlet (9-3) such that upon cessation of fluid flow, the enzyme-nucleotide triphosphate solution beads up into spatially defined droplets (9-4) positioned above each hydrophilic region. An IR source (9-5) through a shaping lens (9-6) projects a beam (9-7) onto a DLP (digital light projection) device (9-8), which is used to simultaneously steer IR beams (9-9) to each of the hydrophobically constrained droplets (9-4) that is chosen to have a specific nucleotide added, resulting in the rapid heating of the polymerase extension reaction formulation to the temperature for maximum enzyme activity for a period of time defined to synthesize a homopolymer of the desired length. After some suitably defined reaction time, the IR source is shut off and a cold rinse buffer is rapidly injected into the flow cell and drained through an outlet (9-10), thus quenching the reaction and finishing one "write" cycle. This series of steps is repeated multiple times for each "write" cycle so that each nascent data strand is randomly accessed according to its spatial location and the chosen nucleotide to be added, until the full length homopolymer data strand is completed. In some embodiments, a DLP device with 1920×1080 steerable mirrors can be used to simultaneously randomly access ~2M synthesis positions in the synthesis flow cell. In some embodiments, the template-independent polymerase used is thermophilic with a reaction temperature optimum well above room temperature, such that enzymatic activity is minimized in the hydrophobically constrained droplets prior to the rapid heating of the droplet by the IR source. In some embodiments, the bottom surface of the flow cell, bearing the hydrophobically defined hydrophilic wells, is abutted to a cooling device that maintains the droplets in the hydrophobic wells at a reduced temperature to prevent enzymatic activity until the temperature is raised by the IR source.

In another embodiment, a flow cell composed of an array of wells that are formed on a suitable substrate by patterning horizontal and vertical stripes of hydrophobic materials forming a plurality of hydrophilic spots bordered by hydrophobic regions. Typical dimensions of the hydrophilic spots can be 300×300 nm to 1000×1000 nm. Each hydrophilic spot is positioned over an individually addressable CMOS heater. This hydrophilic-CMOS heater array forms the floor of a flow cell with a gap of suitable dimensions between the floor and an optically transparent cover. A solution of cold (i.e., below the enzyme-specific temperature optimum) nucleotidyl transferase and one of natural or modified nucleotide triphosphates is flowed into the flow cell such that upon cessation of fluid flow, the polymerase extension reaction solution beads up into spatially defined droplets positioned above each hydrophilic region with an associated CMOS heater. Each of the hydrophobically constrained droplet that is chosen to have a specific nucleotide added is rapidly heated to the temperature for maximum enzyme activity for a period of time defined to synthesize a homopolymer of the desired length. After some suitably defined reaction time, the heater is shut off and a cold rinse buffer is rapidly injected into the flow cell, thus quenching the reaction and finishing one "write" cycle. This series of steps is repeated multiple times for each "write" cycle so that each nascent data strand is randomly accessed according to its spatial location and the chosen nucleotide to be added, until the full length homopolymer data strand is completed. In some embodiments, the enzyme used is thermophilic with a temperature optimum well above room temperature, such that there is a low probability of unwanted nucleotide addition in the hydrophobically constrained drop prior to the rapid heating of the droplet by the CMOS heater.

Figure 10:
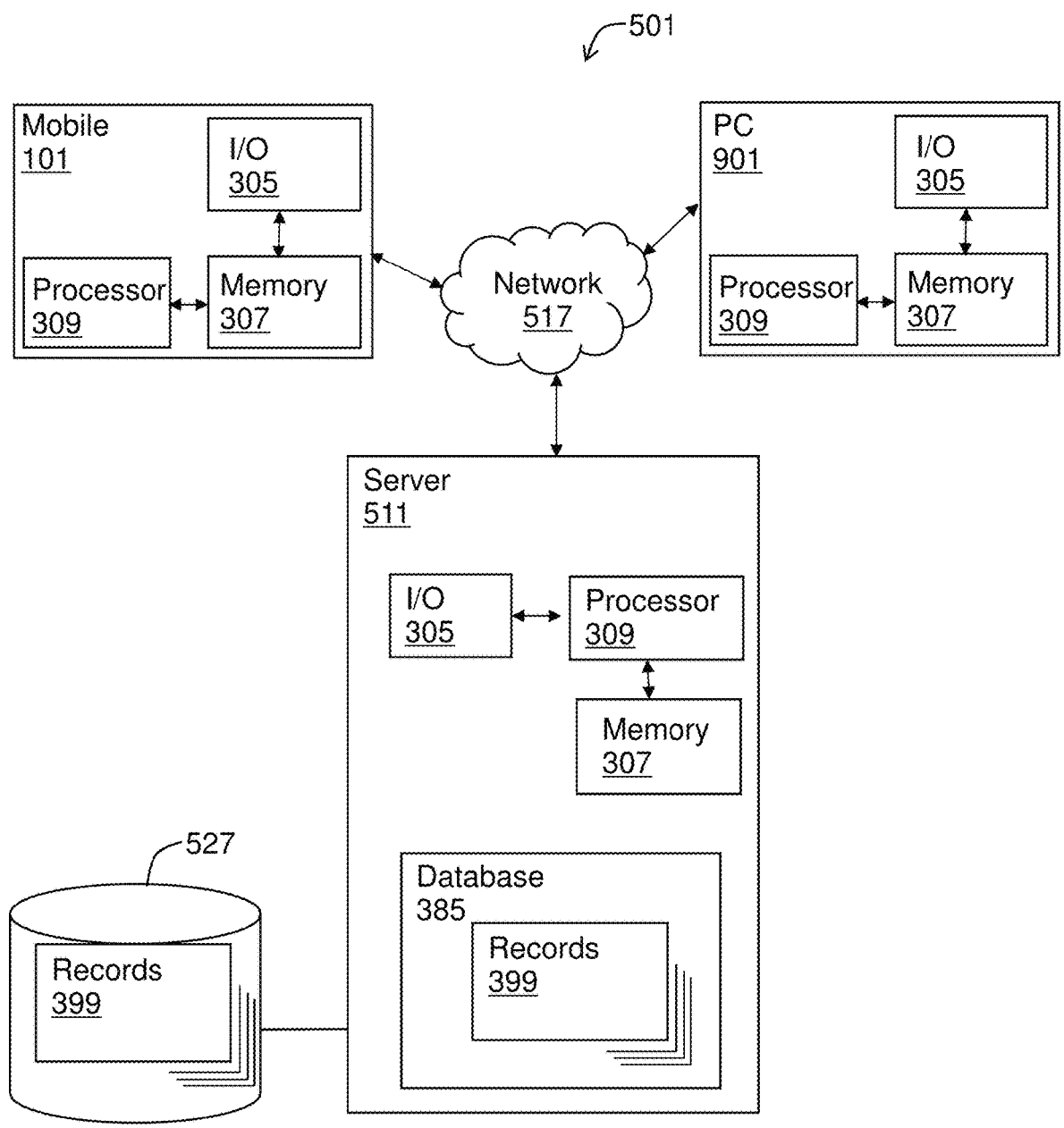
FIG. 10 gives a more detailed schematic of components that may appear within a system.

As one skilled in the art would recognize as necessary or best-suited for the systems and methods of the invention, systems and methods of the invention may include computing devices as shown in FIG. 10 that may include one or more of processor 309 (e.g., a central processing unit (CPU), a graphics processing unit (GPU), etc.), computer-readable storage device 307 (e.g., main memory, static memory, etc.), or combinations thereof which communicate with each other via a bus. Computing devices may include mobile devices 101 (e.g., cell phones), personal computers 901, and server computers 511. In various embodiments, computing devices may be configured to communicate with one another via a network 517.

Computing devices may be used to control the synthesis of memory strands, the reading of sequenced memory strands, and the compiling or translating of data between human or machine-readable formats, digitized data, and nucleic acid sequences among other steps described herein. Computing devices may be used to display the readable format of data.

A processor 309 may include any suitable processor known in the art, such as the processor sold under the trademark XEON E7 by Intel (Santa Clara, Calif.) or the processor sold under the trademark OPTERON 6200 by AMD (Sunnyvale, Calif.).

Memory 307 preferably includes at least one tangible, non-transitory medium capable of storing: one or more sets of instructions executable to cause the system to perform functions described herein (e.g., software embodying any methodology or function found herein); data (e.g., data to be encoded in a memory strand); or both. While the computer-readable storage device can in an exemplary embodiment be a single medium, the term "computer-readable storage device" should be taken to include a single medium or multiple media (e.g., a centralized or distributed database, and/or associated caches and servers) that store the instructions or data. The term "computer-readable storage device" shall accordingly be taken to include, without limit, solid-state memories (e.g., subscriber identity module (SIM) card, secure digital card (SD card), micro SD card, or solid-state drive (SSD)), optical and magnetic media, hard drives, disk drives, and any other tangible storage media.

Any suitable services can be used for storage 527 such as, for example, Amazon Web Services, memory 307 of server 511, cloud storage, another server, or other computer-readable storage. Cloud storage may refer to a data storage scheme wherein data is stored in logical pools and the physical storage may span across multiple servers and multiple locations. Storage 527 may be owned and managed by a hosting company. Preferably, storage 527 is used to store records 399 as needed to perform and support operations described herein.

Input/output devices 305 according to the invention may include one or more of a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, a button, an accelerometer, a microphone, a cellular radio frequency antenna, a network interface device, which can be, for example, a network interface card (NIC), Wi-Fi card, or cellular modem, or any combination thereof.

One of skill in the art will recognize that any suitable development environment or programming language may be employed to allow the operability described herein for various systems and methods of the invention. For example, systems and methods herein can be implemented using Perl, Python, C++, C#, Java, JavaScript, Visual Basic, Ruby on Rails, Groovy and Grails, or any other suitable tool. For a computing device 101, it may be preferred to use native xCode or Android Java.

Figure 11:
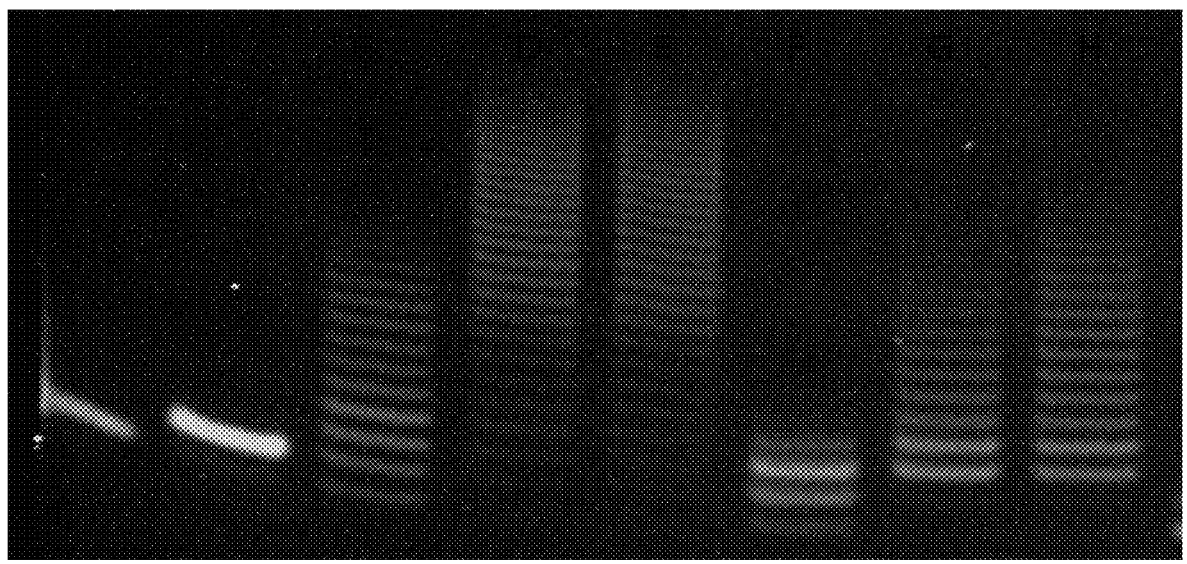
FIG. 11 shows analysis of the enzymatically-mediated synthesis of two different base composition homopolymer tracts.

FIG. 11 shows the polyacrylamide gel electrophoresis analysis of two different single homopolymer tracts made via enzymatic synthesis. Lane A is a sample of a starting 20-mer oligonucleotide that is used in all following lanes. Lane B is a sample from a TdT reaction containing a 20-mer oligonucleotide and the non-reversible terminator ddATP showing the formation of a 21-mer. Lane C is a sample from a TdT reaction containing a 20-mer and the natural nucleotide dATP after 1 minute at 37° C. Lane D is a sample of the same reaction mixture in Lane D after 5 minutes at 37° C. Lane E is a sample of the same reaction mixture in Lane C after 15 minutes at 37° C. Those three lanes illustrate homopolymer length control due to consumption of the input dATP in ~5 minutes during the TdT extension reaction and the observation of no homopolymer growth between 5 and 15 minutes. Lane F is a sample from a TdT reaction containing a 20-mer oligonucleotide and the nucleotide analog N6-benzoyl-dATP after 1 minute at 37° C. Lane G is a sample of the reaction mixture in Lane F after 5 minutes at 37° C. Lane H is a sample of the same reaction mixture in Lane F after 15 minutes at 37° C. Although there are qualitative differences between the length of $dA^{Bz}$ homopolymers formed in Lanes F-H, the same length control is demonstrated even with an N6-modified dATP analog.

Examples $N^6$-benzoyl-deoxyadenosine triphosphate was prepared by charging a vial with $N^6$-benzoyl-2'-deoxyadenosine (0.055 g, 0.16 mmol) under dry $N_2$ and trimethyl phosphate (0.435 mL) was added. To the resulting solution was added tributylamine (0.077 mL, 0.32 mmol) and the reaction mixture was flushed with dry $N_2$ for 30 min while being held at −5° C. To this vial was added anhydrous phosphorous oxychloride (0.018 mL, 0.19 mmol) via syringe and the reaction mixture was stirred at −5° C. for 3 min. A second aliquot of anhydrous phosphorous oxychloride (0.009 mL, 0.10 mmol) was added via syringe and the reaction mixture was stirred at −5° C. for 8 min. A second vial was charged with tributylamine pyrophosphate (0.075 g, 0.14 mmol), flushed with dry $N_2$, and anhydrous acetonitrile was added (0.609 mL), followed by tributylamine (0.231 mL, 0.97 mmol). The prepared tributylamine pyrophosphate mixture was cooled to −20° C. and added to the reaction mixture and allowed to react for 10 m. The reaction was quenched by the dropwise addition of $H_2O$ (4.35 mL). The contents of the flask were combined with 0.87 mL of $H_2O$ and extracted with dichloromethane (3×150 mL). The aqueous phase was adjusted to pH 6.5 with concentrated $NH_4OH$ and stirred for 12 h at 4° C. The mixture was transferred to a 250 mL round bottom flask with 50 mL of water, and concentrated under reduced pressure. The residue was dissolved in 40 mL water, and purified via ion-exchange chromatography (AKTA FPLC, Fractogel DEAE 48 mL column volume, stepwise gradient 0→70% TEAB in water, pH 7.5). Fractions containing the desired product were pooled, the concentration by A260, and concentrated under reduced pressure, with removal of residual triethylammonium bicarbonate via iterative concentration from water (5×50 mL) to dryness to provide $N^6$-benzoyl-2'-deoxyadenosine triphosphate.

Controlled synthesis of homopolymer tracts, comprised of modified nucleotides, by a nucleotidyl transferase, TdT, was conducted in the following manner. Stock solutions of Deoxyadenosine triphosphate (TriLink Biosciences) and $N^6$-benzoyl-deoxyadenosine triphosphate at 1 mM each were prepared in $H_2O$.

0.5 µL (500 pmoles) of each of the different triphosphates was separately combined with 1.5 µL (30 U) of commercially available TdT (Thermo Scientific), 0.5 µL (50 pmoles) of 5'-TAATAATAATAATTTTT-3' (SEQ ID NO: 1) (IDT), 2 µL of commercially available TdT Rxn buffer (Thermo Scientific—1M potassium cacodylate, 0.125M Tris, 0.05% (v/v) Triton X100, 5 mM $C_oCl2$ (pH 7.2 at 25° C.)) and 4.5 µL of H2O. The reactions were incubated at 37° C. 30 µL aliquots were removed after 1 m, 5 m, & 15 m and each quenched with 20 µL 5 mM EDTA. Each sample was dried down under vacuum and reconstituted in 100 µL H2O. 10 µL of each timepoint was mixed with 10 µL of denaturing load buffer (100% formamide and 0.1% Orange G) and applied to the well of a 1 mm×20 cm×14 cm 20% polyacrylamide gel. After electrophoresis at 400 V for 3.5 h, the bands were visualized with Sybr Gold (Thermo Scientific) and photographed under UV illumination (UV-blocking Wratten 2A filter 405 nm cutoff, UVP, LLC).

For synthesis of multiple homopolymer tracts, the initiator oligonucleotide may be attached to a bead to allow multiple rounds of enzymatic synthesis interspersed with removal of the previous reactants and washes. 5'-biotin-TAATAATAATAATTTTT-3' (SEQ ID NO: 1) (IDT) can be incubated with streptavidin coated magnetic sepharose microbeads (GE Healthcare Life Sciences). Oligonucleotide-charged beads can be prepared by removing an aliquot of bead slurry and transferring to filter cup. The beads can then be washed five times with 1×PBS (using 2× volume of bead slurry) vortex and spin down each rinse. ½ bead slurry volume of 1×PBS may then be added, and biotinylated oligonucleotide can be spiked in at ¹/₁₀th published bead binding capacity. The mixture can be incubated at 37 C for 2 hours with vortexing every 30 min. After 2 hours, a small amount of supernatant may be removed and the A260 measured for any unbound oligonucleotide. Once the A260 shows <10% remaining oligonucleotide, the beads can be washed 5× with MQ water. The washed beads can be brought up to a desired concentration in MQ water.

Homopolymer synthesis can be performed as described above using 2-10× molar equivalents of desired dNTP relative to bead bound oligonucleotide. The reaction mixture containing beads, dNTP, TdT and buffer can be incubated at 37° C. for 15 minutes. The reactions may be stopped with 10 µl EDTA and rinsed 3× with water. A new cycle of homopolymer synthesis may be initiated by adding fresh TdT enzyme, dNTP, buffer and incubated at 37° C. for 15 minutes. After stopping the reaction with EDTA and rinsing 3× with water; the cycle of homopolymer synthesis can be repeated as many times as desired. After the last EDTA quench and 3× rinsing with water, the support-bound alternating homopolymers can be cleaved from the solid support using 1000 conc ammonium, and the supernatant dried down by Gen-vac, then stored at −20° C. until ready to be analyzed using a polyacrylamide gel as described above.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method of reading data from a nucleic acid memory strand, the method comprising:
sequencing a nucleic acid memory strand comprising a plurality of homopolymer tracts or heteropolymer tracts, the heteropolymer tracts comprising two or more different nucleotides or nucleotide analogs;
converting the nucleic acid memory strand sequence into digitized data, wherein each of the plurality of homopolymer or heteropolymer tracts represents a bit corresponding to a unit of data,
wherein the homopolymer tracts are converted to bits by identifying transitions between homopolymer tracts, and
wherein the heteropolymer tracts are converted to bits based on a ratio of the two or more different nucleotides or nucleotide analogs to each other within each heteropolymer tract; and
converting the digitized piece of data to a readable format.

2. The method of claim 1, further comprising displaying the readable format.

3. The method of claim 1, wherein the plurality of homopolymer tracts comprises between about 2 and about 10 nucleotide repeats.

4. The method of claim 1, wherein the unit of data is represented in base 2.

5. The method of claim 1, wherein the unit of data is represented in base 3.

6. The method of claim 1, wherein the unit of data is represented in base 4.

7. The method of claim 1, wherein the nucleic acid memory strand is between at least about 200 nucleotides and about 5,000 nucleotides in length.

8. The method of claim 1, wherein the nucleic acid memory strand comprises covalently bound chemical protecting groups that prevent conversion of the nucleic acid memory strand into the dataset, the method further comprising removing one or more of the chemical protecting groups before sequencing the nucleic acid memory strand.

* * * * *

SEQUENCE LISTING

<160> NUMBER OF SEQ ID NOS: 1

<210> SEQ ID NO 1
<211> LENGTH: 17
<212> TYPE: DNA
<213> ORGANISM: Artificial Sequence
<220> FEATURE:
<223> OTHER INFORMATION: Synthesized

<400> SEQUENCE: 1
taataataat aattttt                                                17